United States Patent
Yamada et al.

(10) Patent No.: US 7,449,004 B2
(45) Date of Patent: Nov. 11, 2008

(54) ULTRASONIC TREATMENT DEVICE AND ULTRASONIC TREATMENT SYSTEM

(75) Inventors: Norihiro Yamada, Hachioji (JP);
Haruhiko Ueno, Hachioji (JP);
Hiroyuki Takahashi, Akishima (JP);
Hiroyoshi Watanabe, Kunitachi (JP);
Keita Suzuki, Kokubunji (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 620 days.

(21) Appl. No.: 10/925,374

(22) Filed: Aug. 24, 2004

(65) Prior Publication Data
US 2005/0049525 A1    Mar. 3, 2005

(30) Foreign Application Priority Data
Aug. 28, 2003    (JP)    ............... 2003-304709

(51) Int. Cl.
*A61H 1/00* (2006.01)
*A61B 1/00* (2006.01)
(52) U.S. Cl. ............... 601/2; 600/104; 600/106
(58) Field of Classification Search ............... 600/439, 600/462, 104, 106; 601/2, 3, 213
See application file for complete search history.

(56) References Cited

U.S. PATENT DOCUMENTS

| | | | |
|---|---|---|---|
| 5,139,496 A | | 8/1992 | Hed |
| 6,056,735 A | * | 5/2000 | Okada et al. ............... 606/1 |
| 6,231,578 B1 | | 5/2001 | Rajhansa |
| 6,379,320 B1 | | 4/2002 | Lafon et al. |
| 2003/0225332 A1 | | 12/2003 | Okada |

FOREIGN PATENT DOCUMENTS

| | | |
|---|---|---|
| JP | 8-117240 | 5/1996 |
| JP | 11-56867 | 3/1999 |
| JP | 2000-185052 | 7/2000 |
| JP | 2003-52711 | 2/2003 |

* cited by examiner

*Primary Examiner*—Eric F Winakur
*Assistant Examiner*—Michael T Rozanski
(74) *Attorney, Agent, or Firm*—Scully, Scott, Murphy & Presser, P.C.

(57) ABSTRACT

An ultrasonic transducer unit that generates ultrasonic vibration for treating living tissues has an ultrasonic transducer and a cover member that covers the ultrasonic transducer. A flexible sheath is coupled at one end to the cover member. A signal cable extends through the sheath and is connected at one end to the ultrasonic transducer. A transducer drive unit is connected to the other end of the signal cable. An operation unit is provided at the other end of the flexible sheath.

2 Claims, 8 Drawing Sheets

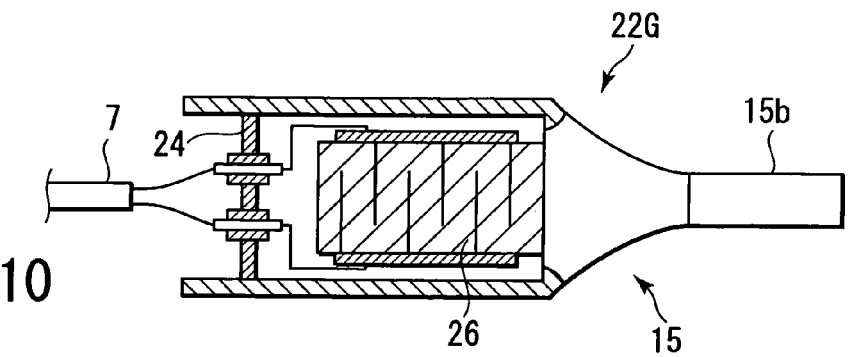
FIG. 10
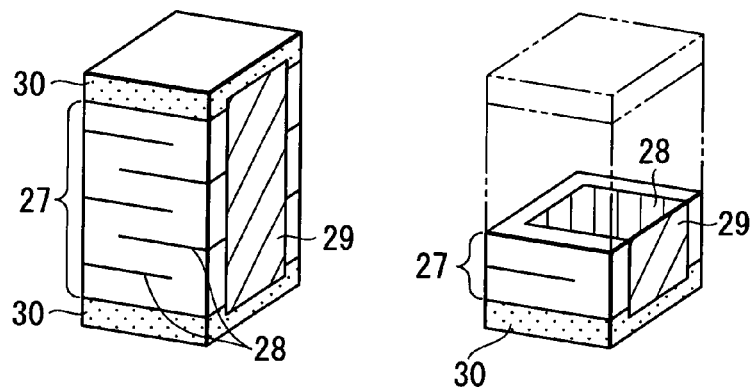
FIG. 11A
FIG. 11B
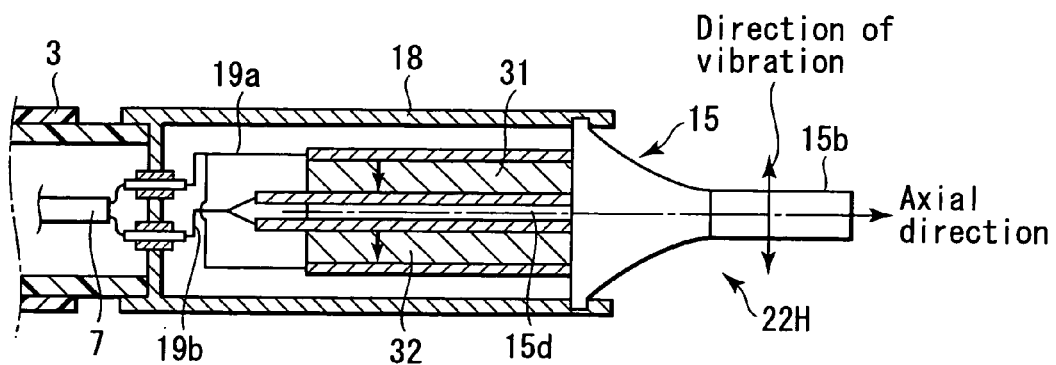
FIG. 12

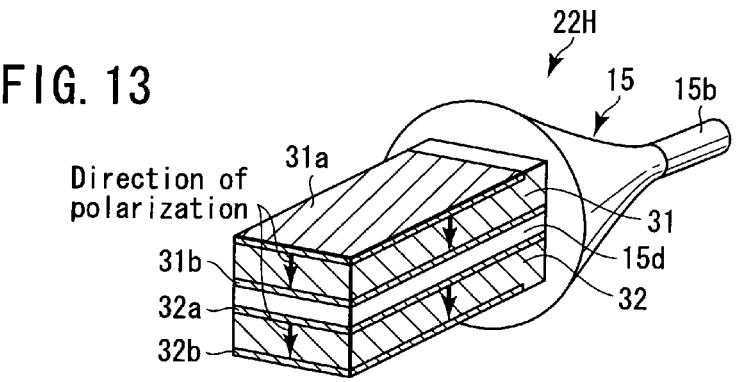
FIG. 13
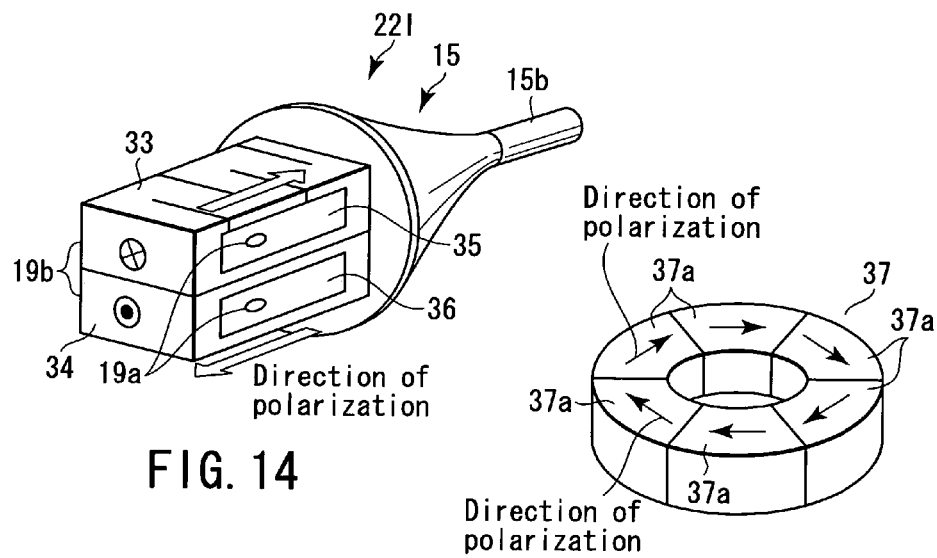
FIG. 14
FIG. 16
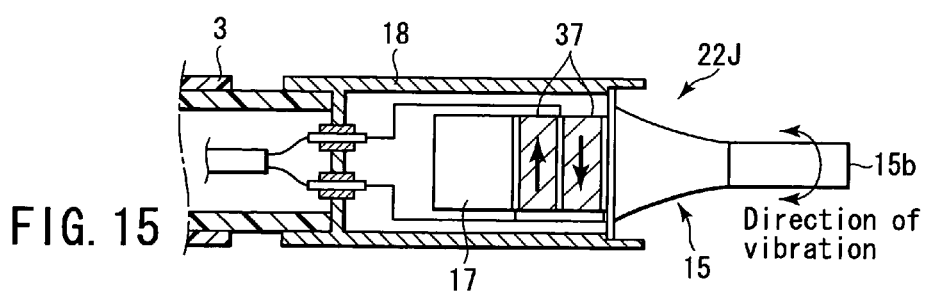
FIG. 15

ULTRASONIC TREATMENT DEVICE AND ULTRASONIC TREATMENT SYSTEM

CROSS-REFERENCE TO RELATED APPLICATIONS

This application is based upon and claims the benefit of priority from prior Japanese Patent Application No. 2003-304709, filed Aug. 28, 2003, the entire contents of which are incorporated herein by reference.

BACKGROUND OF THE INVENTION

1. Field of the Invention

The present invention relates to an ultrasonic treatment device for use in combination with endoscopes, and to an ultrasonic treatment system.

2. Description of the Related Art

U.S. Pat. No. 6,231,578 discloses an ultrasonic treatment device to be inserted into the channel of an endoscope and thereby to be inserted into a patient. This apparatus is guided into the view field of used of the endoscope and used to treat the living tissues in the patient. The apparatus has a flexible wire, a tubular sheath and an operation unit. The flexible wire has a loop on its distal end. The flexible wire extends through the tubular sheath and can slide in the sheath. The operation unit is coupled to the proximal end of the tubular sheath. The operation unit has an actuator and an ultrasonic transducer. The actuator can move the flexible wire in the axial direction of the tubular sheath. The ultrasonic transducer can generate ultrasonic vibration. The ultrasonic vibration generated by the transducer is transmitted to the flexible wire.

When driven, the actuator moves the flexible wire along the axis of the tubular sheath. If the wire is pulled toward the proximal end of the sheath, the loop will go into the sheath and will close. If the wire is pushed toward the distal end of the sheath, the loop will protrude from the sheath and will open. Assume that the loop is wrapped around a tumor such as polyp while it is opening. Also, assume that the wire is pulled toward the proximal end of the sheath. Then, the loop closes and holds the tumor. In this condition, ultrasonic vibration may be transmitted from the ultrasonic transducer to the flexible wire, thereby cutting the tumor.

Jpn. Pat. Appln. KOKAI Publication No. 11-56867 discloses an ultrasonic treatment device. This apparatus is different in structure from the apparatus disclosed in the above-identified U.S. patent. The apparatus has a support rod, an ultrasonic transducer and a blade. The transducer is secured to the distal end of the support rod. The blade is formed integral with the transducer. The apparatus is used, inserted into a body cavity through a trocar. In the body cavity, the blade may cut a target tissue.

BRIEF SUMMARY OF THE INVENTION

According to the invention, there is provided an ultrasonic treatment device that comprises: an ultrasonic transducer unit having an ultrasonic transducer and a cover member which covers the ultrasonic transducer; a flexible sheath having a distal end part and a proximal end part, the distal end part being coupled to the cover member; a signal cable which extends through the sheath and which has a distal end part and a proximal end part, the distal end part being connected to the ultrasonic transducer; a transducer drive unit which is connected to the proximal end part of the signal cable and configured to generate a drive signal for driving the ultrasonic transducer; an operation unit which is provided at the proximal end part of the sheath and configured to move, when operated by a doctor, the sheath in an axial direction to move the ultrasonic transducer unit in the axial direction of the sheath.

Preferably, the ultrasonic transducer has an axis, a main part, a horn and a treatment member. The horn has a distal end part and a proximal end part that is coupled to the main part and is configured to amplify ultrasonic vibration generated by the main part. The ultrasonic vibration is applied to the distal end part. The treatment member is provided at the distal end part of the horn to abut on a living tissue to perform an ultrasonic treatment on the living tissue. The ultrasonic transducer unit has a fastening member. The fastening member secures the cover member at a vibration node of the ultrasonic transducer.

It is desired that the treatment member be located at a ¼-wavelength distance from the fastening member that secures the cover member.

Preferably, the main part of the ultrasonic transducer has a plurality of piezoelectric elements that convert an electric signal to mechanical vibration, a plurality of electrodes that supply an electric signal to the piezoelectric elements, and a connecting plate; the cover member is positioned preferably at the vibration node of the ultrasonic transducer and interposed between the horn and the piezoelectric elements; and the ultrasonic transducer unit has an embedded bolt that fastens the horn, cover member, piezoelectric elements, electrodes and connecting plate to one another.

It is desired that the horn and the cover member be formed integral with each other in the ultrasonic transducer unit.

Preferably, the main part of the ultrasonic transducer has piezoelectric layers, inner electrodes and outer electrodes, which are alternately, laid one upon another.

Preferably, the ultrasonic transducer has a main part. The main part is a transverse vibrator that vibrates in a direction perpendicular to the axis of the ultrasonic transducer.

It is desired that the ultrasonic transducer should have a torsional-vibration main part that vibrates in a circle around the axis.

It is preferred that the signal cable should have a connector at the proximal end part. The connector can be connected to the transducer drive unit.

Preferably, the operation unit has a cable-guiding port through which the signal cable is guided, and the signal cable thus guided is connected to the transducer drive unit.

It is preferred that the signal cable should have a connector at an end part which protruding from the cable-guiding port. The connector can be connected to the transducer drive unit.

It is desired that the ultrasonic transducer unit should have a forceps member that s rotatably coupled to the cover member; the forceps member should have support pins that are rotatably supported by the cover member and a holding part that contacts and leaves the horn when rotated around the support pins; an operation wire should extend through the flexible sheath to operate the forceps member and has a proximal end part and a distal end part which is connected to the forceps member; and the operation unit should have a guide portion that extends in the axial direction of the operation wire and a handle that is mounted on the guide portion so as to be moved back and forth and which is connected to the proximal end part of the operation wire to pull and slacken the operation wire, thereby to move the forceps member to and from the horn.

It is desired that the signal cable should have a connector at the proximal end part, and that the connector should be able to be connected to the transducer drive unit.

It is desired that the forceps member be supported to clamp a living tissue between the holding part and the proximal end part of the horn.

Preferable, the ultrasonic transducer unit has a pair of forceps members that are arranged at two sides of the horn, respectively, and which are rotatably coupled to the cover member; the forceps members have a support pin and a holding part each, the support pin being rotatably coupled to the cover member and the holding part contacting and leaving the horn as the forceps member is rotated around the support pin; and each of the forceps members is supported such that a living tissue is clamped between the holding part and the horn.

According to this invention there is provided an ultrasonic treatment system that has an ultrasonic treatment device, and an endoscope used in combination with the ultrasonic treatment device. The ultrasonic treatment device comprises: an ultrasonic transducer unit having an ultrasonic transducer designed to treat a living tissue, and a cover member that covers the ultrasonic transducer; a flexible sheath that has a distal end part and a proximal end part, the distal end part being coupled to the cover member; a signal cable that has a distal end part and a proximal end part, the distal end part being connected to the ultrasonic transducer; a transducer drive unit that is connected to the proximal end part of the signal cable and designed to generate a drive signal for driving the ultrasonic transducer; an operation unit that is provided at the proximal end part of the sheath and designed to move the sheath, thereby to move the ultrasonic transducer unit in an axial direction of the sheath. The endoscope includes an elongate insertion unit that is to be inserted into a body cavity and has at least one channel. The cover member and flexible sheath of the ultrasonic treatment device have outside diameters smaller than the inside diameter of the channel of the endoscope. The ultrasonic transducer unit is designed to move into and from the channel of the endoscope when the operation unit is moved in the axial direction of the sheath.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10 is a longitudinal sectional view depicting the ultrasonic transducer used in a sixth modification of the first embodiment;

FIG. 11A is a perspective view representing the multi-layered piezoelectric element used in the ultrasonic transducer incorporated in the modification shown in FIG. 10;

FIG. 11B is a perspective view representing another type of a multi-layered piezoelectric element that may be used in the ultrasonic transducer incorporated in the modification shown in FIG. 10;

FIG. 12 is a longitudinal sectional view showing the ultrasonic transducer used in a seventh modification of the first embodiment;

FIG. 13 is a perspective view depicting the plate-shaped vibrating member of the ultrasonic transducer shown in FIG. 12;

FIG. 14 is a perspective view illustrating the ultrasonic transducer provided in an eighth modification of the first embodiment;

FIG. 15 is a perspective view showing the ultrasonic transducer provided in a ninth modification of the first embodiment;

FIG. 16 is a perspective view depicting the torsional-vibration piezoelectric element incorporated in the ultrasonic transducer shown in FIG. 15;

DETAILED DESCRIPTION OF THE INVENTION

First Embodiment

Figure 1:
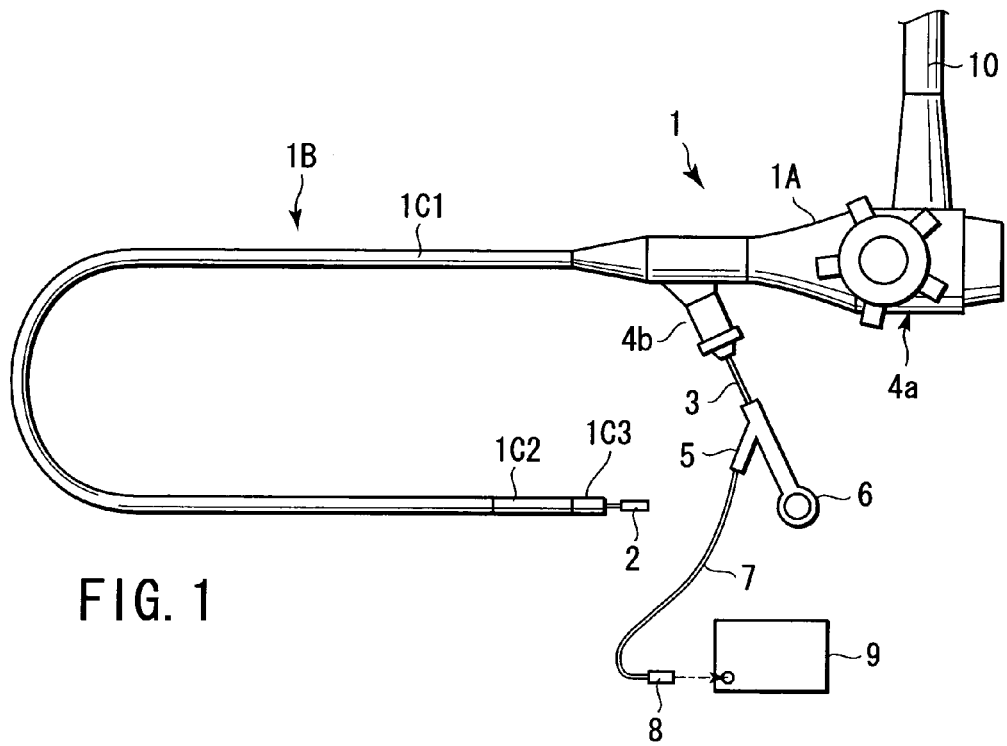
FIG. 1 is a schematic representation of an endoscope that has an ultrasonic treatment device according to a first embodiment of this invention.

FIGS. 1 to 4 shows the first embodiment of the present invention. FIG. 1 is a schematic representation of an endoscope 1 that may be used in combination with an ultrasonic treatment device 2. The endoscope 1 has an insertion unit 1B and an operation unit 1A. The insertion unit 1B is a long tube that may be inserted into a tubular cavity in the subject. The operation unit 1A is coupled to the proximal end of the insertion unit 1B. The insertion unit 1B has a tubular portion 1C1, a bending portion 1C2, and a distal end portion 1C3. The flexible tubular portion 1C1 is a long flexible tube. Its proximal end is coupled to the operation unit 1A. The bending portion 1C2 is connected at one end to the distal end of the tubular portion 1C1. The distal end portion 1C3 is connected to the other end of the bending portion 1C2.

Figure 2:
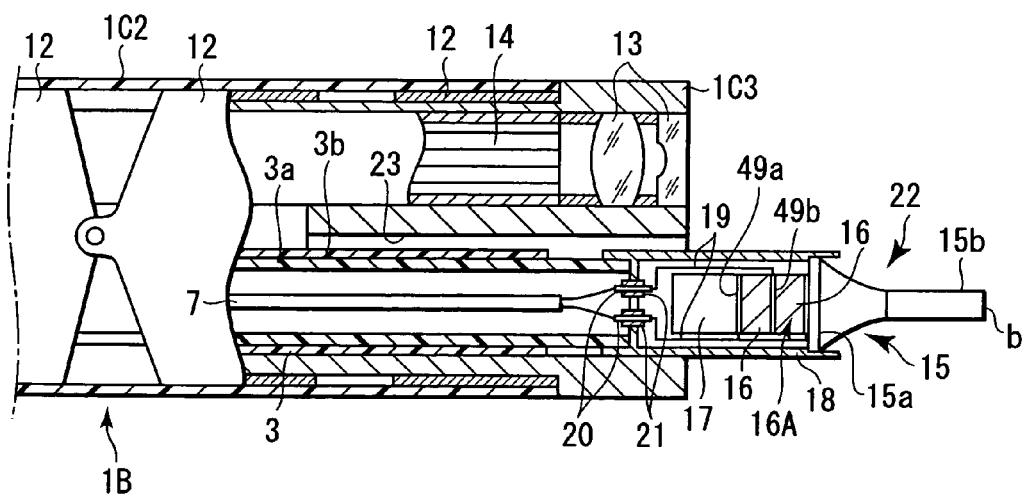
FIG. 2 is a magnified sectional showing the distal end portion of the endoscope and the distal end portion of the ultrasonic treatment device.

As FIG. 2 shows, the bending portion 1C2 contains a plurality of segments 12. The segments 12 are arranged in the axial direction of the bending portion 1C2. They are coupled so that each may rotate with respect to the adjacent ones. Wires (not shown) extend through the tubular portion 1C1 and the bending portion 1C2. The wires are connected at one end to the segments 12, respectively, and at the other end to the operation unit 1. They can be pulled and slackened as the operation unit 1 is operated, to rotate the segments 12. If the segments 12 are so rotated, the bending portion 1C2 will be bent.

Figure 3A:
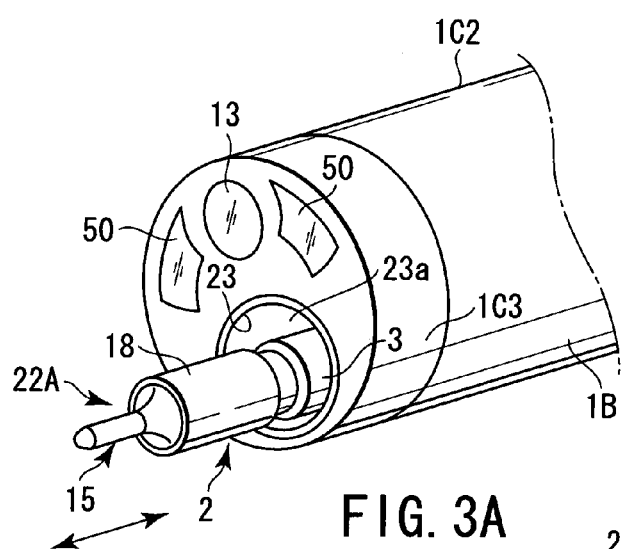
FIG. 3A is a perspective view depicting the distal end portion of the endoscope and that of the ultrasonic treatment device.

As FIG. 3A shows, an observation lens (observation means) 13 and two illumination lenses (illumination means) 50 are provided in the distal end of the distal end portion 1C3. The distal end 23a of a channel 23 opens at the distal end of the distal end portion 1C3. As illustrated in FIG. 2, an image guide 14 has its distal end lying behind the observation lens 13 and opposing this lens 13. An imaging element such as a CCD may be arranged at the back of the observation lens 13, more precisely at the focus of the lens 13. Then, the imaging element can convert the image of an object formed by the lens 13 into an electric signal. At the back of the illumination lenses 50, the distal end of a light guide (not shown) is positioned, opposing both illumination lenses 50.

The insertion unit 1B contains an image guide, the light guide (not shown), and the channel 23, in addition to the wires (not shown) to be operated to bend the bending portion 1C2. Note that the image guide may be replaced by a signal cable if an imaging element is arranged at the back of the observation lens 13.

The operation unit 1A has a tube-bending knob 4a and a cap 4b. The tube-bending knob 4a is coupled to a bending mechanism (not shown) that is incorporated in the operation unit 1A. It is to this bending mechanism that the wires for bending the bending portion 1C2 are connected. As the knob 4a is rotated, the wires are pulled and slackened to rotate the segments 12 and, hence, bend the bending portion 1C2.

The channel 23 has its proximal end coupled to the cap 4b. From the cap 4b, various treatment devices, such as forceps, the ultrasonic treatment device 2 and the like, can be inserted into the channel 23. Any treatment device thus inserted into the channel 23 may protrude from the distal end 23a of a channel 23.

A universal code 10 is connected, at one end, to the operation unit 1A. At the other end, the universal code 10 has a connector, which is connected to a light source (not shown) and a video camera (not shown, either).

The ultrasonic treatment device 2, i.e., the first embodiment of the invention, has a flexible sheath 3, an operation unit 6, and an ultrasonic transducer unit 22A. The operation unit 6 is coupled to the proximal end of the flexible sheath 3. The ultrasonic transducer unit 22A is coupled to the distal end of the flexible sheath 3.

The flexible sheath 3 is a double-layer tube. The double-layer tube is composed of an inner layer 3a and an outer layer 3b. A reinforcing member is interposed between the inner layer 3a and the outer layer 3b. Alternatively, the reinforcing member may be embedded in either the inner layer 3a or the outer layer 3b. The ultrasonic transducer unit 22A is inserted in the flexible sheath 3.

As seen from FIG. 2, the ultrasonic transducer unit 22A has an ultrasonic transducer 16A and a hollow-cylindrical transducer cover (cover member) 18. The ultrasonic transducer 16A has a piezoelectric element (transducer body) 16, a negative (−) electrode 49a, a positive (+) electrode 49b, a horn 15, and a connecting plate 17. The horn 15 has a flange 15a and a treatment member 15b. The flange 15a lies at a node of vibration. The treatment member 15b has its distal face b located at the anti-node of vibration. The connecting plate 17 is made of metal and firmly secures the treatment member 15b to that end of the horn 15 that opposes the flange 15a.

The transducer cover 18 covers the entirety of the ultrasonic transducer 16A, except the horn 15. The transducer cover 18 has two holes in the rear end, into which electrically conductive pins can be inserted.

Two electrically conductive pins 20 project backwards from the proximal end of the ultrasonic transducer 16A. These conductive pins 20 are inserted in the two holes made in the rear end of the transducer cover 18, respectively. An insulating sheath 21 is provided on each electrically conductive pin 20. The sheath 21 fills the gap between the electrically conductive pin 20 and the hole made in the transducer cover 18.

Each electrically conductive pin 20 is connected, at inner end, coupled to one end of a conductor 19 that supplies electric power to the piezoelectric element 16. The two conductors 19 are connected, at the other end, to the negative (−) electrode 49a and positive (+) electrode 49b of the piezoelectric element 16, respectively.

The transducer cover 18 is connected to the flexible sheath 3. The transducer cover 18 and the flexible sheath 3 have almost the same outside diameter. The diameters of the transducer cover 18 and flexible sheath 3 are smaller than the inside diameter of the channel 23. The ultrasonic transducer unit 22A and the flexible sheath 3 can therefore pass through the channel 23.

The flexible sheath 3 is a little longer than the channel 23. The ultrasonic transducer unit 22A can therefore protrude from, and recede into, the distal end portion 1C3 of the endoscope 1, when the operation unit 6 is moved back and forth.

The above-mentioned signal cable 7 is connected, at distal end, to the outer ends of both electrically conductive pins 20. The signal cable 7 extends through the flexible sheath 3, reaching the operation unit 6. The signal cable 7 has its proximal end portion extending outwards through a cable outlet port 5. To the proximal end of the signal cable 7 there is connected a connector 8 at one end. The connector 8 is connected, at the other end, to a transducer drive unit 9. The ultrasonic transducer unit 22A can receive drive signals from the transducer drive unit 9.

Figure 3B:
FIG. 3B is a side view showing the knife-shaped distal end of a horn that may be mounted on the ultrasonic transducer incorporated in the ultrasonic treatment device.
Figure 3C:
FIG. 3C is a side view showing the hook-shaped distal end of a horn that may be mounted on the ultrasonic transducer.

The treatment member 15b of the horn 15 may be a knife-shaped one 15b1 shown in FIG. 3B or a hook-shaped one shown in FIG. 3C. The member 15b may have any other type, nonetheless, so long as it can perform its function. As FIG. 2 depicts, the front b of the treatment member 15b is located at an anti-node of vibration. The flange 15a secured to the transducer cover 18 is positioned at a node of vibration. The front b of the treatment member 15b is spaced from the flange 15a by a distance of ¼ wavelength.

Figure 4:
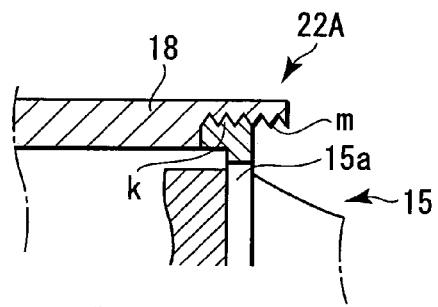
FIG. 4 is a longitudinal sectional view illustrating how the horn is fitted in the transducer cover in the ultrasonic treatment device according to the first embodiment.

FIG. 4 illustrates how the horn 15 is fitted in the transducer cover 18. The flange 15a of the horn 15 is relatively long in the axis of the horn 15. The flange 15a has a male screw k cut in its peripheral surface. The transducer cover 18 has a female screw m cut in the inner peripheral surface of its distal end portion. The male screw k meshes with the female screw m. Thus, the flange 15a of the horn 15 is secured to the transducer cover 18.

How the ultrasonic treatment device 2, which is the first embodiment of the invention, operates will be described. To use the ultrasonic treatment device 2, the doctor inserts the insertion unit 1B of the endoscope 1 (FIG. 1) into a tubular body cavity of the subject, first the distal end portion 1C3 of the insertion unit 1B. The doctor inserts the insertion unit 1B, while observing an image of the body-cavity interior, obtained through the observation lens 13 and displayed on a video monitor. Note that the interior of the body cavity is illuminated with the light applied through the illumination lenses 50. After locating an effected tissue in the body cavity, the doctor inserts the ultrasonic treatment device 2 into the body cavity through the cap 4b of the operation unit 1A.

More specifically, the doctor first inserts the horn 15, then the transducer cover 18 and finally the flexible sheath 3, into the channel 23 through the cap 4b. At this time, the doctor moves the operation unit 6 back and forth, bringing the treatment member 15b on the horn 15 to the affected tissue that should be treated. Then, the doctor moves the operation unit 6 again, causing the treatment member 15b to contact the affected tissue.

Then, the doctor turns on a switch (not shown) to generate ultrasonic vibration. More precisely, he or she turns on a foot switch or a hand switch. While the switch remains on, a drive signal is supplied from the transducer drive unit 9 via the signal cable 7 to the piezoelectric element 16 of the ultrasonic transducer unit 22A. The piezoelectric element 16 converts the drive signal, i.e., an electric signal, to ultrasonic vibration. The ultrasonic vibration propagates to the horn 15. Hence, the treatment member 15b provided at the distal end of the horn 15 applies the ultrasonic vibration to the affected tissue. The tissue is thereby crushed, is emulsified or is coagulated to stop bleeding.

Configured as described above, the ultrasonic treatment device 2 is advantageous in some respects. First, the transducer cover 18 covering the horn 15 and the flexible sheath 3 coupled to the cover 18 have outside diameters smaller than the inside diameter of the channel 23 of the endoscope 1. Second, once the ultrasonic transducer unit 22A has been inserted into the channel 23, the treatment member 15b provided at the distal end of the horn 15 can protrude from, and receded into, the distal end of the channel 23 as the operation unit 6 is moved back and forth. Therefore, the treatment member 15b can cut or coagulate the living tissue while it is undergoing ultrasonic vibration.

In addition, the doctor can cut or coagulate a living tissue by touching the tissue with the treatment member 15b undergoing ultrasonic vibration. Thus, the doctor can cut tumors relatively large and tumors not projecting, can cut the blood vessels and can stop bleeding at such tumors and the blood vessels. In other words, the ultrasonic treatment device 2 can be used to accomplish various medical treatments in body cavities.

Further, the flexible sheath 3 can be deformed in the same way as the bending portion 1C2 of the endoscope 1, because the ultrasonic transducer unit 22A is coupled to the distal end of the flexible sheathe 3 that is a long tube. This makes it possible to bend the portion 1C2 of the endoscope 1 smoothly and makes it easy to project the treatment member 15b from, and pull it into, the distal end portion 1C3 of the endoscope 1.

Moreover, the components of the ultrasonic transducer 16A, such as the piezoelectric element 16, are not exposed since the hollow cylindrical transducer cover 18 covers all the components of the transducer 16A, except the horn 15. This renders the ultrasonic treatment device 2 safer to the subject.

Figure 5:
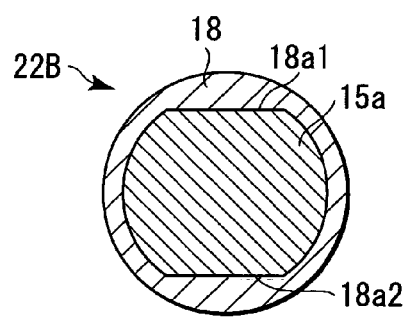
FIG. 5 is a transverse sectional view showing how the horn is fitted in the transducer cover in a first modification of the first embodiment.

FIG. 5 shows a first modification of the ultrasonic transducer unit 22A that is incorporated in the ultrasonic treatment device 2, i.e., the first embodiment of this invention. In this modified transducer unit 22B, the horn 15 is secured to the transducer cover 18 by laser welding. That is, a laser beam is applied to the interface between the flange 15a and the transducer cover 18, thereby welding the horn 15 to the transducer cover 18. As FIG. 5 shows, the flange 15a has flat surfaces and the cover 18 has flat inner surfaces 18a1 and 18a2. These flat surfaces make it easy to position the horn 15 and the cover 18 with respect to each other in preparation for the laser welding.

Figure 6:
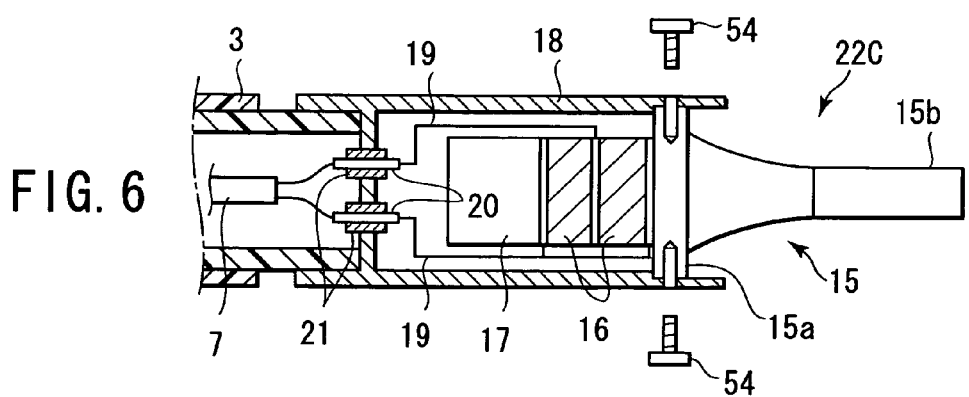
FIG. 6 is a longitudinal sectional view showing how the horn is fitted in the transducer cover in a second modification of the first embodiment.

FIG. 6 depicts a second modification of the ultrasonic transducer unit 22A that is incorporated in the ultrasonic treatment device 2, i.e., the first embodiment of this invention. In the second modified transducer unit 22C, the horn 15 is secured to the transducer cover 18 by means of screws. More precisely, screws 54 are driven into the flange 15 though the holes made in the transducer cover 18, thus fastening the flange 15a to the transducer cover 18.

Figure 7:
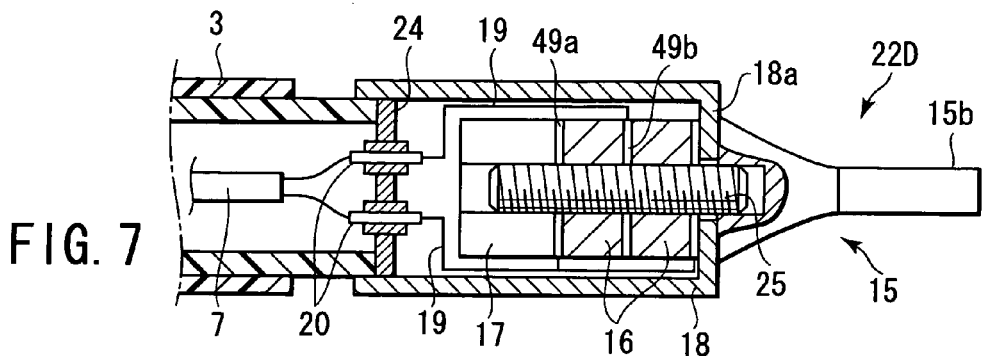
FIG. 7 is a longitudinal sectional view showing how the horn is fitted in the transducer cover in a third modification of the first embodiment.

FIG. 7 depicts a third modification of the ultrasonic transducer unit 22A that is incorporated in the ultrasonic treatment device 2, i.e., the first embodiment of this invention. In this modified transducer unit 22D, the distal end portion of the transducer cover 18 is bent, forming a bent part 18a. The bent part 18a is clamped between the horn 15 and the piezoelectric element 16. An embedded bolt 25 fastens the horn 15, transducer cover 18, piezoelectric element 16, electrodes 46a and 46b and connecting plate 17 to one another. Thus, the components of the transducer unit 22D can be fastened together and the transducer cover 18 can be secured, by using one bolt only, i.e., the embedded bolt 25.

Figure 8:
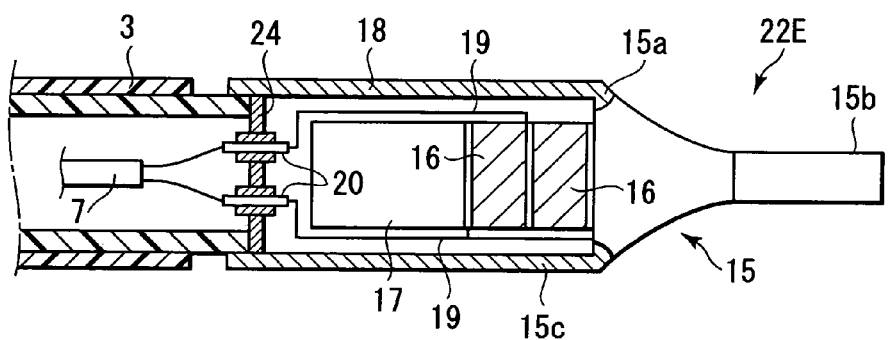
FIG. 8 is a longitudinal sectional view showing how the horn is fitted in the transducer cover in a fourth modification of the first embodiment.

FIG. 8 shows a fourth modification of the ultrasonic transducer unit 22A that is incorporated in the ultrasonic treatment device 2, i.e., the first embodiment of this invention. In the fourth modified transducer unit 22E, the horn 15 has a hollow cylindrical cover 15c that is formed integral with the rear end. Thus, the horn 15 functions not only as a horn, but also as a transducer cover 18. In other words, one component works as two components. This simplifies the structure of the transducer unit. The rear end of the hollow cylindrical cover 15c is closed with a shield plate 24. The shield plate 24 has two holes that guide the electrically conductive pins 20.

Figure 9:
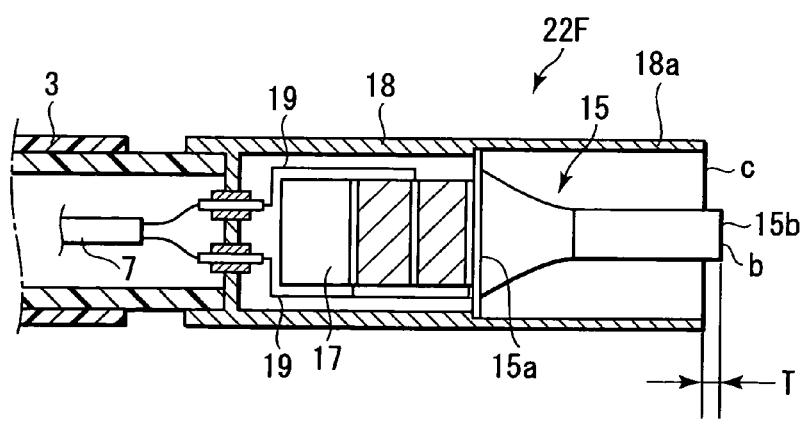
FIG. 9 is a longitudinal sectional view illustrating the ultrasonic transducer provided in a fifth modification of the fist embodiment.

FIG. 9 illustrates a fifth modification of the ultrasonic transducer unit 22A that is incorporated in the ultrasonic treatment device 2, i.e., the first embodiment of this invention. In the fifth modified transducer unit 22F, a hollow cylinder 18a is formed integral with the rear end of the transducer cover 18. The hollow cylinder 18a extends forwards from the flange 15a the horn 15. The distance T between the distal end c of this cylinder 18a and the distal end b of the horn 15 can be adjusted to provide a desired depth of treatment. This meets the demand that the treatment member 15b should be located at a specific depth in some methods of treating affected tissues.

FIG. 10 shows a sixth modification of the ultrasonic transducer unit 22A that is incorporated in the ultrasonic treatment device 2, i.e., the first embodiment of this invention. In the transducer units 22A to 22F described above, the horn 15, piezoelectric element 16, electrodes 49a and 49b and connecting plate 17 are fastened together with a bolt, constituting a langevin transducer. The sixth modified transducer unit 22G is different in that the piezoelectric element 26 is adhered to the horn 15 as is illustrated in FIG. 10. Hence, the sixth modified transducer unit 22G has a more simple structure.

FIG. 11A shows the multi-layered piezoelectric element 26 used in the sixth modified transducer unit 22G. The multi-layered piezoelectric element 26 is composed of one outer electrode 29 and two insulating protective layers 30, which have been formed integral by means of sintering. When supplied with an electric signal, the piezoelectric element 26 vibrates at ultrasonic frequency.

FIG. 11B depicts another type of a multi-layered piezoelectric element 26 for use in the sixth modified ultrasonic transducer 22G. This multi-layered piezoelectric element 26 is composed of a piezoelectric layer 27, one inner electrode 28, one outer electrode 29 and one insulating protective layer 30, which have been formed integral by means of sintering.

The ultrasonic transducer unit 22A and the modified ultrasonic transducer units 22B to 22G vibrate in their axial direction, performing longitudinal vibration. Other vibration may be more effective than longitudinal vibration in some cases, depending on the shape and condition of the tissue to be treated.

FIGS. 12 and 13 illustrate a seventh modification 22H of the ultrasonic transducer unit 22A that is incorporated in the ultrasonic treatment device 2, i.e., the first embodiment of this invention. The seventh modified transducer unit 22H can vibrate in the direction perpendicular to the axial direction, thus achieving transverse vibration.

The ultrasonic transducer unit 22H shown in FIGS. 12 and 13 has an element-supporting member 15d integrally formed with the rear end of the horn 15. The element-supporting member 15d is shaped like a plate and extends in the axial direction of the horn 15. Two vibrators 31 and 32, either shaped like a plate, are mounted on the upper and lower surfaces of the element-supporting member 15d. The plate-shaped vibrators 31 and 32 oppose each other across the element-supporting member 15d.

As FIG. 13 shows, a negative (−) electrode 31b is interposed between the plate-shaped vibrator 31 and the element-supporting member 15d, and a negative (−) electrode 32a is interposed between the plate-shaped vibrator 32 and the element-supporting member 15d. Two positive (+) electrodes 31a and 32b are mounted on the outer surfaces of the vibrators 31 and 32, respectively. The plate-shaped vibrators 31 and 32 are therefore polarized in the direction of arrows as illustrated in FIGS. 12 and 13.

A negative (−) conductor 19b is connected to the negative (−) electrodes 31b and 32a that contact the element-supporting member 15d. A positive (+) conductor 19a is connected to the positive (+) electrodes 31a and 32b that oppose the transducer cover 18. Thus connected, the conductors 19a and 19b serve to generate transverse vibration. Transverse vibration works well to crush, for example, stones in body cavities.

FIG. 14 shows an eighth modification 22I of the ultrasonic transducer unit 22A that is incorporated in the ultrasonic treatment device 2, i.e., the first embodiment of this invention. The eighth modified transducer unit 22I has two multi-layered piezoelectric elements 33 and 34 that are can adhere to the horn 15. As indicated by the arrows in FIG. 14, the multi-layered piezoelectric elements 33 and 34 are polarized in the opposite directions. A positive (+) conductor 19a is connected to one external electrode 35 of the element 33 and one external electrode of the element 34, and a negative (−) conductor 19b is connected to the other external electrode (not shown) of the element 33 and the other external electrode (not shown) of the element 34. Hence, the modified transducer unit 22I generates transverse vibration.

FIGS. 15 and 16 show a ninth modification 22J of the ultrasonic transducer unit 22A that is incorporated in the ultrasonic treatment device 2, i.e., the first embodiment of this invention. The ninth modified transducer unit 22J has two torsional-vibration transducers 37 that are shaped like a ring. As FIG. 16 depicts, each torsional-vibration transducer 37 is composed of segments 37a. It has been made by cutting a ring into segments 37a, polarizing each segment 37a in the direction indicated by an arrow in FIG. 16, and bonding the segments 37 to each other to form a ring.

As seen in FIG. 15, the torsional-vibration transducers 37 are fastened to the horn 15 such that they are polarized in the opposite directions. Hence, the ninth modified transducer unit 22J can generate torsional vibration in the circumferential direction of the transducers 37.

Figure 17:
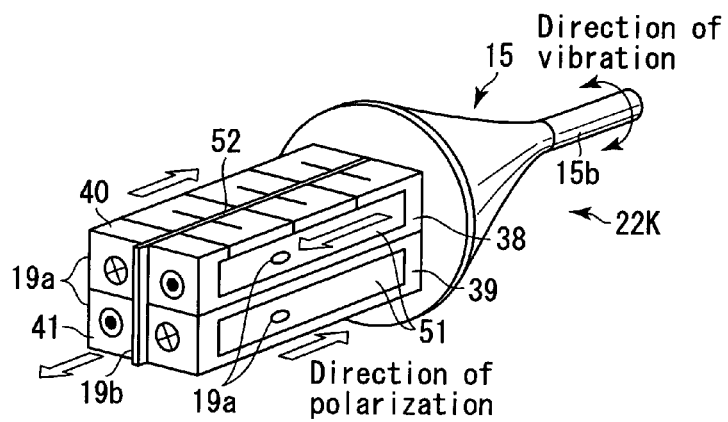
FIG. 17 is a perspective view showing the ultrasonic transducer provided in a tenth modification of the first embodiment.

FIG. 17 illustrates a tenth modification 22K of the ultrasonic transducer unit 22A that is incorporated in the ultrasonic treatment device 2, i.e., the first embodiment of this invention. The ninth modified transducer unit 22K has four multi-layered piezoelectric elements 38 to 41. The piezoelectric elements 38 to 41 are polarized in the directions of the arrows shown in FIG. 17. The piezoelectric elements 38 to 41 are arranged, opposing one another. Four outer electrodes 51 amounted on the piezoelectric elements 38 to 41 are connected to a positive (+) conduct or 19a. Two negative (−) electrodes 52 interposed, respectively, between the piezoelectric elements 38 and 39 and between the piezoelectric elements 40 and 41. Both negative (−) electrodes 52 are connected to a negative (−) conductor 19b. The modified transducer unit 22K can therefore generate vibration.

Second Embodiment

Figure 18:
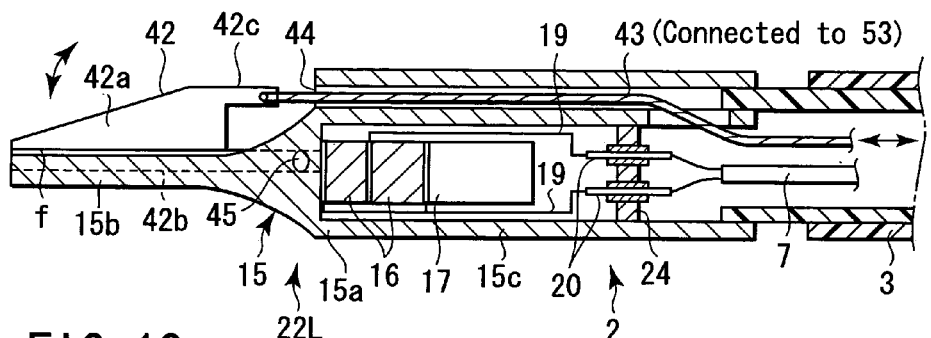
FIG. 18 is a longitudinal sectional view illustrating the distal end portion of an ultrasonic treatment device according to a second embodiment of the invention.
Figure 19:
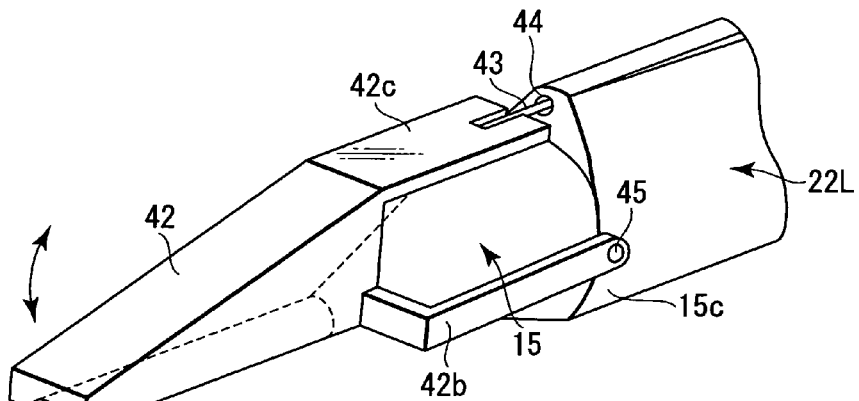
FIG. 19 is a perspective view showing the distal end portion of the second embodiment.
Figure 20:
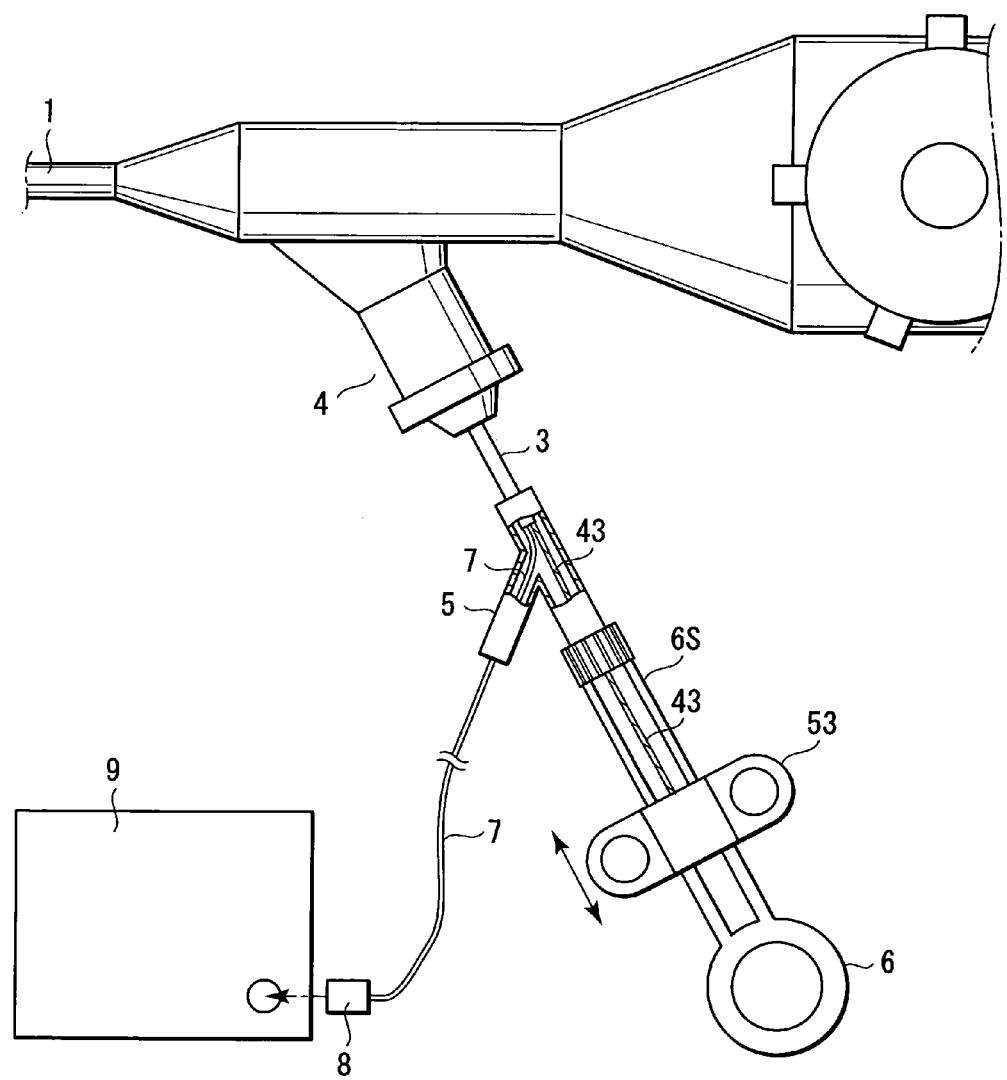
FIG. 20 is a side view of the operation unit and handle of the second embodiment, the handle shown with a part cut away.

FIGS. 18 to 20 show a second embodiment of this invention. The components that are identical to those of the first embodiment will be designated at the same reference numerals and will not be described. Only the components different from those of the first embodiment will be described.

As FIGS. 18 and 19 depict, the ultrasonic treatment device according to the second embodiment has a flexible sheath 3, an ultrasonic transducer unit 22L, and a forceps 42. The transducer unit 22L is coupled to the distal end of the flexible sheath 3. It has a horn 15, which in turn has a treatment member 15b. The forceps 42 is attached to the distal end of the ultrasonic transducer unit 22L. The forceps 42 has a holding part 42a, a rear end part 42c, and a supporting part 42b. The holding part 42a has a holding surface f that may contact the treatment member 15b of the horn 15. The rear end portion 42c is formed integral with the rear end of the holding part 42a. The supporting part 42b is provided on one side of the holding part 42a and formed integral with the holding part 42a.

An operation wire 43 is connected, at one end, to the rear end portion 42c. The horn 15 has a hole 44, through which the operation wire 43 passes. A cover 15c is formed integral with the rear end of the treatment member 15b. The cover 15c performs the same function as the transducer cover 18 that has been described with reference to FIG. 2. Note that in the first embodiment, the transducer cover 18 may have a hole through which an operation wire can pass.

The hole 44 is made in the cover 15c that is integral with the rear end of the treatment member 15b. The operation wire 43 passes through the cap 4b of an endoscope 1 and extends to the operation unit 6 of the endoscope 1, as is illustrated in FIG. 20. The operation wire 43 is connected, at proximal end, to a handle 53.

As FIG. 19 shows, support pins 45 couples the supporting part 42b of the forceps 42 to the cover 15c of the horn 15, allowing the supporting part 42b to rotate. The handle 53 can slide in the axial direction of the shaft portion 6S of the operation unit 6.

When the handle 53 is pushed and pulled, the operation wire 43 moves the rear end portion 42c of the forceps 42 back and forth. So moved, the wire 43 rotates the forceps 42 around the support pins 45, in the direction of the arrows shown in FIG. 19. As a result, the holding part 42a of the forceps 42 can open and close.

How the second embodiment is used will be explained. At first, the doctor inserts the distal end portion 1C3 of the endoscope 1 into the tubular cavity in the subject. In this process, light is applied to the wall of the cavity from the illumination lenses 50. Thus, the doctor can observe the interior of the cavity on the video monitor. After locating an affected tissue in the cavity, the doctor inserts the ultrasonic treatment device 2 from the cap 4b of an endoscope 1 into the tubular cavity. At this time, the forceps 42 remains closed, abutting on the treatment member 15b of the horn 15. The doctor inserts first the cover 15C and then the flexible sheath 3, from the cap 4b into the channel 23 of the endoscope 1.

To insert the ultrasonic treatment device 2 into the tubular cavity, the doctor moves the handle 53 forth, while observing the interior of the cavity through the endoscope 1. After the device 2 enters the cavity, the doctor moves the handle 53 forth further, until the treatment member 15b of the horn 15 abuts on the affected tissue to be treated. Note that the horn 15 is attached to the distal end of the transducer unit 22L.

Thereafter, the doctor pulls the handle 53 and rotates the handle 53, opening the forceps 42. That is, the holding part 42a of the forceps 42 moves away from the treatment member 15b of the horn 15. Then, the doctor pushes the operation unit 6, maintaining the forceps 42 open. The affected living tissue is thereby clamped between the treatment member 15b and the holding part 42a.

After clamping the tissue, the doctor turns on the switch (a foot switch or a hand switch) to generate ultrasonic vibration. Then, a drive signal is supplied from the transducer drive unit 9 via the signal cable 7 to the piezoelectric element 16 of the ultrasonic transducer unit 22A. The piezoelectric element 16 converts the drive signal, i.e., an electric signal, to ultrasonic vibration. The ultrasonic vibration propagates to the treatment member 15b of the horn 15. The doctor pushes the handle 53, clamping the living tissue between the treatment member 15b and the holding part 42a. Now clamped between the treatment member 15b and the holding part 42a, the living tissue can be crushed, emulsified or coagulated to stop bleeding as the treatment member 15b at the distal end of the horn 15 undergoes ultrasonic vibration.

Configured as described above, the second embodiment is advantageous in some respects. The flexible sheath 3 can be deformed in the same way as the bending portion 1C2 of the endoscope 1 is bent, because the ultrasonic transducer unit 22L is coupled to the distal end of the flexible sheath 3. So deformed, the sheath 3 would not hinder the bending of the portion 1C2 of the endoscope 1. In addition, the treatment member 15b provided at the distal end of the horn 15 can easily protrude from, and receded into, the distal end of the channel 23 as the doctor moves the handle 53 back and forth on the operation unit 6.

Furthermore, the first embodiment enables the doctor to apply ultrasonic vibration to a living tissue reliably, because the forceps 42 and the treatment member 15b can clamp the living tissue.

Third Embodiment

Figure 21:
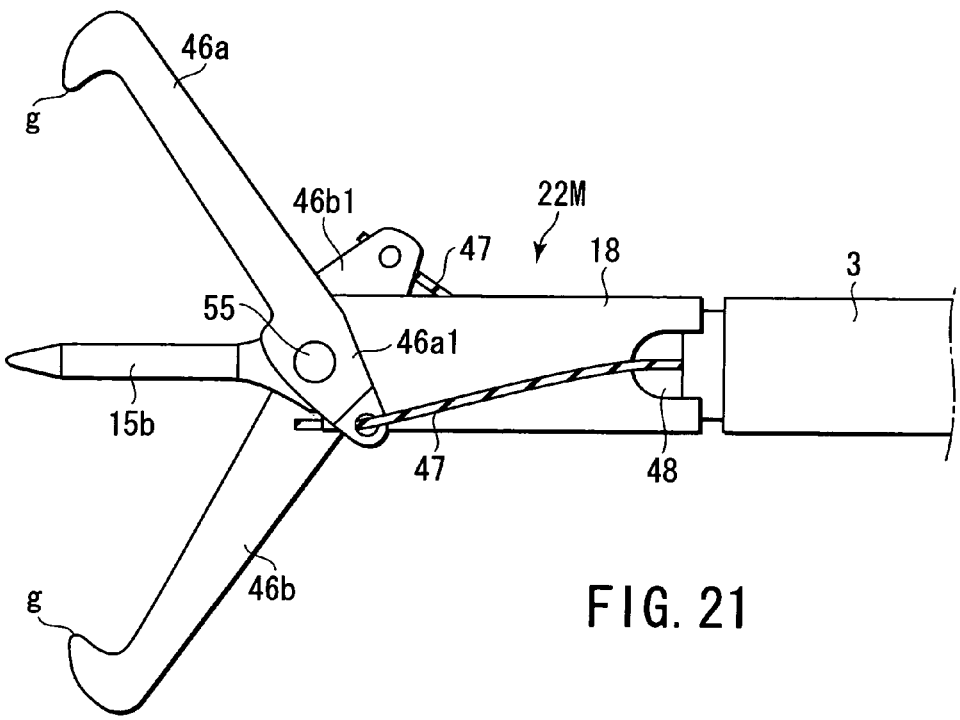
FIG. 21 is a front view of the distal end portion of an ultrasonic treatment device according to a third embodiment of the present invention.
Figure 22:
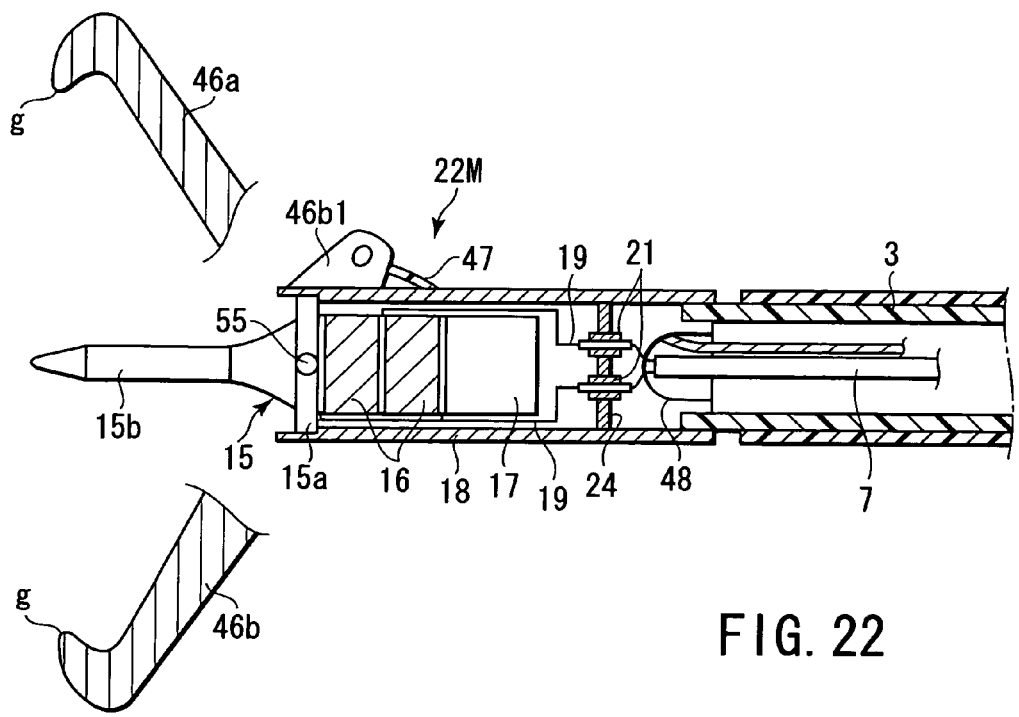
FIG. 22 is a longitudinal sectional view illustrating the distal end portion of the ultrasonic treatment device according to the third embodiment.

FIG. 21 and 22 illustrate an ultrasonic treatment device that is a third embodiment of the present invention. The components that are identical to those of the first embodiment will be designated at the same reference numerals and will not be described. Only the components different from those of the first embodiment will be described.

The ultrasonic treatment device, i.e., the third embodiment, has a flexible sheath 3, an ultrasonic transducer unit 22M, a transducer cover 18, and two (a pair of) forceps 46a and 46b. The ultrasonic transducer unit 22M is coupled to the distal end of the flexible sheath 3. The forceps 46a and 46b have a claw g each at the free end. They have rear end parts 46a1 and 46b1, respectively. Two support pins 55 couple the rear end part 46a1 and 46b1 to the transducer cover 18, allowing the forceps 46a and 46b to rotate.

Two operation wires 47 are fastened to the rear end part 46a1 of the forceps 46a and the rear end part 46b1 of the forceps 46b, respectively. The wires 47 are inserted into the flexible sheath 3 through the U-notches 48 cut in the transducer cover 18. The wires 47 extend through the flexible sheath 3 and are connected to the handle 53 (FIG. 20) provided on the operation unit 6 of an endoscope.

The handle 53 can slide back and forth on the shaft portion 6S of the operation unit 6. When the handle 53 is moved back and forth, the operation wires 47 are moved back and forth. As the wires 47 are so moved, the forceps 46a and 46b rotate around the support pins 55 in the opposite directions. Thus, the claws g at the distal ends of the forceps 46a and 46b can open and close the treatment member 15b.

How to operate the third embodiment will be described. First, the doctor inserts the distal end portion 1C3 of the endoscope 1 into the tubular cavity in the subject. In this process, light is applied to the wall of the cavity from the illumination lenses 50. Thus, the doctor can observe the interior of the cavity on the video monitor. After locating an affected tissue in the cavity, the doctor inserts the ultrasonic treatment device 2 from the cap 4b of an endoscope 1 into the tubular cavity. At this time, the forceps 46a and 46b of the device 2 are held in the closed position. The doctor inserts the horn 15, the forceps 46a and 46b, the transducer cover 18 and the flexible sheath 3, in the order they are mentioned, from the cap 4b into the channel 23 of the endoscope 1.

To insert the ultrasonic treatment device 2 into the tubular cavity, the doctor moves the handle 53 forth, while observing the interior of the cavity through the endoscope 1. After the device 2 enters the cavity, the doctor moves the handle 53 forth further, until the treatment member 15b of the horn 15 abuts on the affected tissue to be treated. It should be noted that the horn 15 is attached to the distal end of the transducer unit 22M.

Thereafter, the doctor pulls the handle 53 and rotates the handle 53, opening the forceps 46a and 46b. Namely, the forceps 46a and 46b moves away from the treatment member 15b of the horn 15. Then, the doctor pushes the operation unit 6, maintaining the forceps 46a and 46b open. The affected living tissue is thereby clamped between the claws g of the forceps 46a and 46b.

After clamping the tissue, the doctor turns on the switch (a foot switch or a hand switch) to generate ultrasonic vibration. Then, a drive signal is supplied from the transducer drive unit 9 via the signal cable 7 to the piezoelectric element 16 of the ultrasonic transducer unit 22A. The piezoelectric element 16 converts the drive signal, i.e., an electric signal, to ultrasonic vibration. The ultrasonic vibration propagates to the treatment member 15b of the horn 15. The doctor further pulls the handle 53, squeezing the living tissue between the claws g of the forceps 46a and 46b. Thus, the living tissue can be cut or coagulated to stop bleeding as the treatment member 15b undergoes ultrasonic vibration.

Configured as described above, the second embodiment is advantageous in some respects. The flexible sheath 3 can be deformed in the same way as the bending portion 1C2 of the endoscope 1 is bent, because the ultrasonic transducer unit 22M is coupled to the distal end of the flexible sheath 3. So deformed, the sheath 3 would not hinder the bending of the portion 1C2 of the endoscope 1. Moreover, the treatment member 15b provided at the distal end of the horn 15 of the unit 22M can easily protrude from, and receded into, the distal end portion 1C3 of the endoscope 1 as the doctor moves the handle 53 back and forth on the operation unit 6.

Since the forceps 46a and 46b can reliably clamp the living tissue, the third embodiment makes it easier for the doctor to perform ultrasonic treatment on the living tissue as is desired.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment system having an ultrasonic treatment device, and an endoscope used in combination with the ultrasonic treatment device, said ultrasonic treatment device comprising:

an ultrasonic transducer unit having an ultrasonic transducer designed to treat a living tissue, and a cover member which covers the ultrasonic transducer;

a flexible sheath which has a distal end part and a proximal end part, the distal end part being coupled to the cover member;

a signal cable which has a distal end part and a proximal end part, the distal end part being connected to the ultrasonic transducer;

a transducer drive unit which is connected to the proximal end part of the signal cable and designed to generate a drive signal for driving the ultrasonic transducer;

an operation unit which is provided at the proximal end part of the sheath and designed to move the sheath, thereby to move the ultrasonic transducer unit in an axial direction of the sheath, wherein the endoscope includes an elongate insertion unit which is to be inserted into a body cavity and which has at least one channel, the cover member and flexible sheath of the ultrasonic treatment device have outside diameters smaller than the inside diameter of the channel of the endoscope, and the ultrasonic transducer unit is designed to move into and from the channel of the endoscope when the operation unit is moved in the axial direction of the sheath;

the ultrasonic transducer has an axis, a main part, a horn and a treatment member, the horn having a distal end part and a proximal end part which is coupled to the main part, and being configured to amplify ultrasonic vibration generated by the main part, which is applied to the distal end part, and the treatment member being provided at the distal end part of the horn to abut on a living tissue to perform an ultrasonic treatment on the living tissue; and the ultrasonic transducer unit has a fastening member which secures the cover member at a vibration node of the ultrasonic transducer.

2. The device according to claim 1, wherein the treatment member is located at a ¼-wavelength distance from the fastening member which secures the cover member.

* * * * *